United States Patent [19]
Moorhead

[11] Patent Number: 5,865,764
[45] Date of Patent: Feb. 2, 1999

[54] DEVICE AND METHOD FOR NONINVASIVE MEASUREMENT OF INTERNAL PRESSURE WITHIN BODY CAVITIES

[75] Inventor: William D. Moorhead, West University Place, Tex.

[73] Assignee: Armoor Opthalmics, Inc., Houston, Tex.

[21] Appl. No.: 774,632

[22] Filed: Dec. 30, 1996

[51] Int. Cl.$^6$ .................................................. A61M 05/00
[52] U.S. Cl. .......................................... 600/561; 600/563
[58] Field of Search ........................... 73/861.42, 861.64; 600/561, 563, 488, 486, 487, 489; 604/131

[56] References Cited

U.S. PATENT DOCUMENTS

| | | |
|---|---|---|
| 4,041,947 | 8/1977 | Weiss . |
| 4,210,029 | 7/1980 | Porter ........................................ 73/705 |
| 4,548,205 | 10/1985 | Armeniades et al. ................... 600/561 |
| 4,722,350 | 2/1988 | Armeniades . |
| 4,823,552 | 4/1989 | Ezell et al. ................................ 60/443 |
| 4,841,984 | 6/1989 | Armeniades . |
| 5,141,493 | 8/1992 | Jacobsen et al. ......................... 604/29 |
| 5,322,504 | 6/1994 | Doherty . |
| 5,399,166 | 3/1995 | Laing ...................................... 604/131 |

OTHER PUBLICATIONS

Moorhead, L.C. and Armeniades, C.D. "The Pressure–Controlled Infusion System... "Ophthalmic surgery1988: vol. 19, pp. 282–287.

Gardner, T.W. et al. "Intraocular Pressure Fluctuation During Scleral Buckling Surgery." Ophthamology7/93: vol. 100(7): pp. 1050–1054.

Witherspoon, C.D. et al.: "Automatic Regulation of Fluid Infusion Pressure during Vitrectomy." Archives of Ophthalmology, 1986: vol 104, p.1551.

Blumenthal, M. et al.: "Effect of Continuous Positive Intraocular Pressure . . . " Developments in Ophthalmology1991: vol. 22: 119–121.

Mayer, H.M. "Spine Update. Percutaneous Lumbar Disc Surgery. " Spine, 12/94: vol. 19(23), pp. 2719–2723.

Diaz–Buxo, J.A. et al. "Automated Peritoneal Dialysis. " From The TextBook of Peritoneal Dialysis, 1994. pp. 399–418. Kluwer Academic Publishers, Norwell, Ma, USA.

Primary Examiner—Robert L. Nasser
Attorney, Agent, or Firm—R. Perry McConnell

[57] ABSTRACT

A device and method for determining internal fluid pressure in a body cavity during irrigation procedures is presented. The invention relies on noninvasive measurements on a calibrated surgical apparatus to determine the dynamic internal fluid pressure. Once the dynamic internal fluid pressure is known, a control signal can be generated to indicate needed changes to pressure-regulating equipment, such as a pump.

40 Claims, 3 Drawing Sheets

5,865,764

DEVICE AND METHOD FOR NONINVASIVE MEASUREMENT OF INTERNAL PRESSURE WITHIN BODY CAVITIES

FIELD OF THE INVENTION

The invention concerns accurate, noninvasive measurement of internal pressure within body cavities.

BACKGROUND OF THE INVENTION

Physicians and surgeons employ procedures involving infusion of a fluid into a body cavity ("irrigation procedures"). Irrigation procedures are often used in conjunction with removal of fluid, unwanted material, diseased tissue, or waste products via aspiration. As used herein, "irrigation procedures" refers to procedures or methods involving delivery of irrigation fluid into a body cavity, regardless of whether aspiration is also performed.

When using irrigation procedures, it is desirable to be able to measure and control the fluid pressure within the body cavity. Lack of control over the internal pressure may impair the effectiveness or ease of the procedure, and in certain cases may result in damage to tissue. The ability to adjust the fluid pressure within the cavity may also be used to control bleeding.

Some examples of irrigation procedures are intraocular surgery, peritoneal dialysis, and removal of diseased spinal disc material. In intraocular surgery, failure to maintain sufficient fluid pressure during an operation may result in collapse of the eyeball with concomitant tissue damage. Conversely, over-pressuring the intraocular region may also result in damage to the sensitive retinal, optic nerve, or corneal tissue. However, it is occasionally desirable to apply controlled high pressure for a brief time period, for example, to staunch bleeding in the intraocular region. If it is necessary or desirable to alter the pressure within the body cavity, the surgeon needs the ability to rapidly alter the pressure to a desired value without significant deviations from that value.

Peritoneal dialysis is used with patients suffering from kidney failure. In peritoneal dialysis, clean fluid is irrigated into the peritoneal (abdominal) cavity and fluid containing waste substances is aspirated out. If abnormally high pressure develops in the peritoneal cavity, mass transfer of waste substances into the dialysis fluid and normal blood flow will likely be disrupted.

Similarly, patients suffering from degenerative lumbar disc disease may have diseased disc tissue removed by irrigation procedures. Surgeons removing this tissue make a small incision through the skin, allowing insertion of a needle-like instrument into the appropriate disc space. The instrument is used to cut away diseased tissue. Irrigation fluid aids in flushing the cut material into an aspiration line. Accurate pressure control is likely to enhance the ease and effectiveness of this procedure.

Attempts to measure and control pressure in irrigation procedures have met with limited success. These attempts have usually related to intraocular surgery. Such surgery involves operations on or within the vitreous cavity or the anterior segment cavity of an eye. As used herein, "anterior segment cavity" means that portion of an eye comprising the anterior chamber and the posterior chamber. Most types of intraocular surgery utilize irrigation procedures. Dedicated surgical machines and highly specialized tools have been developed for such surgery. Cataract surgery (the removal of opacified lens tissue) employs an invasive tool which is used in the anterior segment cavity of an eye. This tool usually contains an irrigation outlet, a mechanical or ultrasonic cutter, and an inlet to an aspiration line, all in close proximity. Alternatively, a separate tool may be used to provide aspiration. Vitrectomy (the excision and removal of tissue from the vitreous) usually involves two invasive tools: an irrigation cannula, which is inserted into the globe and temporarily attached to the sclera, and a cutting/aspiration tool that is manipulated by the surgeon.

One method of controlling pressure within the eye during surgery is disclosed in U.S. Pat. No. 4,041,947 to Weiss, et al. That patent discloses the use of limiting valves external to the eye on the infusion and aspiration lines. These limiting valves are designed to provide pressure relief if either the pressure in the infusion line exceeds a high limit, or if the pressure in the aspiration line exceeds a low limit. This device does provide some ability to maintain pressure within a predetermined range of values, but does not allow the surgeon to accurately know or set the intraocular pressure ("IOP"), nor does it necessary allow rapid correction of over- or under-pressure conditions.

It is possible to directly measure the intraocular pressure ("IOP") in this type of surgery by insertion of a pressure transducer into the eye. U.S. Pat. Nos. 4,548,205, 4,722,350, and 4,841,984 to Armeniades, et al., disclose direct measurement and control of the IOP. A pressure transducer is inserted into the eye as an independent tool or integrated into the cutting tool. Alternatively, a pressure transducer can be integrated into a separate tool that provides infusion or aspiration.

However, there are several problems with tools which provide direct measurement of the IOP. If the pressure transducer is incorporated into the invasive portion of a tool, the tool must be made larger in diameter than is necessary to perform the actual surgery. This approach requires a correspondingly larger incision in the eyeball for tool insertion. Further, integration of a pressure transducer into another tool creates inaccuracies in the pressure readings caused by the proximity of the transducer to the operating infusion line, aspiration line, or surgical tool.

One solution to the size problem is to design a tool with a channel which is inserted into the eye and which provides fluid communication with a pressure transducer outside of the eye. However, this design suffers from the same accuracy problems detailed above, as well as problems caused by debris from the operation clogging the channel. This accuracy problem can be overcome by providing a separate tool that only contains a pressure transducer for insertion into the eye away from the operating tools. However, this approach is disfavored because it requires another incision into the eye.

Similarly, irrigation procedures on other body cavities in which internal fluid pressure must be controlled have characteristic constraints regarding tool size and a need to limit the number of incisions.

It is an object of the invention to provide a device and method for noninvasively measuring internal fluid pressure in a body cavity during irrigation procedures.

It is another object of the invention to provide a control signal for a pressure-generating device, such as a pump, to allow for automatic control of the dynamic internal fluid pressure in a body cavity.

SUMMARY OF THE INVENTION

The invention is a device and method for noninvasively determining and providing for automatic control of fluid pressure within a body cavity during irrigation procedures. The invention relies on pressure or flow measurements taken outside of the body cavity to determine the value of the internal fluid pressure.

Specifically, the apparatus includes a source of irrigation fluid, such as saline. The irrigation fluid is used to replace the volume of fluid that is removed from the body cavity. The irrigation fluid source is generally a fluid reservoir, such as a bottle. The reservoir may be raised to a specific height to produce a base level of infusion pressure. Because it is desirable to dynamically control the infusion pressure, irrigation fluid from the reservoir is preferably directed into a controllable pump via a pump inlet line. The pump inlet line is in fluid communication with the reservoir and with the controllable pump.

The output of the controllable pump is in fluid communication with an infusion line. The infusion line comprises a first end and a second end. The output of the controllable pump is directed into the first end of the infusion line. The second end of the infusion line includes an outlet for flow of the irrigation fluid into the body cavity. The infusion line outlet is insertable into the body cavity. A portion of the infusion line may also be inserted into the body cavity to properly position the infusion line outlet. Further, a return line is placed in fluid communication with the infusion line and the pump inlet line. The return line aids in buffering pressure fluctuations in the infusion line and also provides a source of hydrostatic pressure from the reservoir in the event of a pump failure. One or more compliance chambers may be placed in fluid communication with the infusion line or the return line to reduce pressure fluctuations from sources such as the pump rollers.

The irrigation procedure within the body cavity is accomplished by insertion of the infusion line outlet into the body cavity. If surgery is to be performed within the body cavity, a surgical tool or cutting instrument is also inserted into the body cavity. Removal of tissue or fluid from within the body cavity is accomplished by providing an aspiration line, which is in fluid communication with the body cavity. The aspiration line comprises a first end and a second end. The first end of the aspiration line comprises an inlet for receiving tissue and fluid. The aspiration line inlet is insertable into the body cavity. A portion of the aspiration line may also be inserted into the body cavity to properly position the aspiration line inlet within the body cavity. The second end of the aspiration line is in fluid communication with a vacuum source. A waste reservoir in fluid communication with the aspiration line may be used to collect removed tissue and fluid.

The body cavity internal fluid pressure ("IFP"), the pressure at the outlet end of the infusion line, is measured by utilizing two sensors. If the two sensors are both pressure transducers, the first sensor is placed at a first point along the infusion line, and the second sensor is placed at a second point along the infusion line, downstream of the first pressure sensor. "Downstream of the first sensor" as used here means at a location between the first sensor and the body cavity, but physically exterior to the body cavity. It is preferred that no compliance chambers be connected to the infusion line downstream of the first sensor. Alternatively, one sensor may be a pressure sensor and the other sensor a flow rate sensor. If a flow rate sensor is used, it may be placed at or near the pressure sensor or at some other location along the infusion line. Each pressure sensor that is used is attached to the infusion line so that it measures the irrigation fluid pressure inside the infusion line at the point of attachment. If a flow rate sensor is used, it is attached to the infusion line so that it measures the irrigation fluid flow rate inside the infusion line.

The apparatus may be considered to be a system of interconnected fluid carriers (lines) meeting at points called junctions. Such systems through which the fluid flow to a given junction may come from several different lines are called a network of lines and are, in many ways, analogous to electrical networks. The following conditions must be satisfied in a network of lines. (Streater and Wylie "Fluid Mechanics" ch 11, 8th edition, McGraw-Hill Inc., New York, 1985.):

1) The algebraic sum of the pressure drops around each closed circuit must be zero; and 2) The fluid flow rate into each junction must equal the fluid flow rate out of each junction.

Because of the overall size of the apparatus, transients will propagate through the apparatus in a time on the order of a few milliseconds. This propagation time is very small in comparison to the time associated with the pressure fluctuations present in the apparatus. Accordingly, in a section of line with no branches, the fluid flow rate can be considered to be the same at a given instant of time at all points of that section. Thus on the basis of fundamental dimensional arguments such as those found in article 366 of Lamb's "Hydrodynamics", it is inferred that, over a reasonable range of fluid flow rates, each section of the infusion pathway will obey a power-law relation between the fluid flow rate at the two points and the pressure drop between those points.

If two pressure transducers are used, the pressure measured by the first pressure transducer at a given time is designated as "$P_{up}$." The pressure measured by the second pressure transducer at the same time is designated as "$P_{down}$." The IFP at the same time is designated as "$P_{ifp}$." Using "I" to represent the irrigation fluid flow rate at the given time in the infusion line, one can write the equations:

$$P_{up} - P_{down} = a_1 I^{b_1} \quad (1)$$

$$P_{down} - P_{ifp} = a_2 I^{b_2} \quad (2)$$

Solving these equations for I, and combining the resulting equations yields an expression for $P_{ifp}$:

$$P_{ifp} = P_{down} - a\{P_{up} - P_{down}\}^b \quad (3)$$

Equation (3) provides a means of determining the IFP by measuring $P_{up}$ and $P_{down}$, assuming the values of the parameters a and b are known.

Experimental determination of the fitting parameters a and b is made using the apparatus described above within a test cavity which is sufficiently similar to the actual body cavity to provide accurate values for a and b. For example, in the case of intraocular surgery, the parameters a and b may be determined by using a human cadaver eye. The actual IFP is measured by inserting an additional pressure transducer into the intraocular region of the cadaver eye. Controlled variation of the source pressure is provided by the controllable pump. Each pressure sensor provides a signal to a filter, which in turn relays the filtered signal to an Analog to Digital ("A/D") converter. Output from the A/D converter is read by computer and recorded. Simultaneous measurement of $P_{up}$, $P_{down}$, and $P_{ifp}$ over a range of source pressures provides a set of data from which the fitting parameters a and b can be determined by use of well-known numerical methods. The numerical determination of the fitting parameters a and b is made easier by taking the logarithm of Equation (3) to produce an equation that is linear in log(a) and b:

$$\log \{P_{down}-P_{ifp}\}=\log (a)+b \log \{P_{up}-P_{down}\} \quad (4)$$

Experiments with a variety of human cadaver eyes have shown that the fitting parameters a and b are effectively constants for all human eyes for a particular surgical apparatus. This fact allows human cadaver eyes to be used for the determination of the fitting parameters a and b for a particular apparatus. Careful manufacture of the surgical apparatus will insure that the flow characteristics, and therefore the values of the fitting parameters a and b, will remain constant for each apparatus constructed. It is noted that the fitting parameters a and b vary for a given surgical apparatus between types of eyes, i.e., human cadaver eyes, pig eyes, and a model eye consisting of a fluid-filled sphere.

It will be apparent to one skilled in the art that the measurements external to the body cavity do not necessarily have to both be pressure measurements. Specifically, a combination of a pressure measurement and a flow rate measurement results in an equation for $P_{ifp}$ based on $P_0$ and I, where $P_0$ is the single pressure measurement and I is the measured flow rate:

$$P_{ifp}=P_0-cI^d \quad (5)$$

Again, experimental data collected using a test cavity and measuring the actual IFP allows numerical fitting to find values of the fitting parameters c and d for the irrigation apparatus.

Once the appropriate fitting parameters for the surgical apparatus are determined, the system may be used to control the IFP during an irrigation procedure. Signals from the sensors are provided to a computation device, such as a computer, allowing real-time computation of the IFP. This computed result is compared to a desired set-point, allowing the computer to further determine whether the controllable pump's operation should be maintained or altered. An appropriate control circuit from the computer to the controllable pump allows the computer to dynamically control the IFP. The computer can dynamically generate a control signal based on the difference between the current IFP and the desired IFP. If the operator desires a change in the IFP, the set-point can be altered by input to the computer.

DETAILED DESCRIPTION OF THE PREFERRED EMBODIMENT

Figure 1:
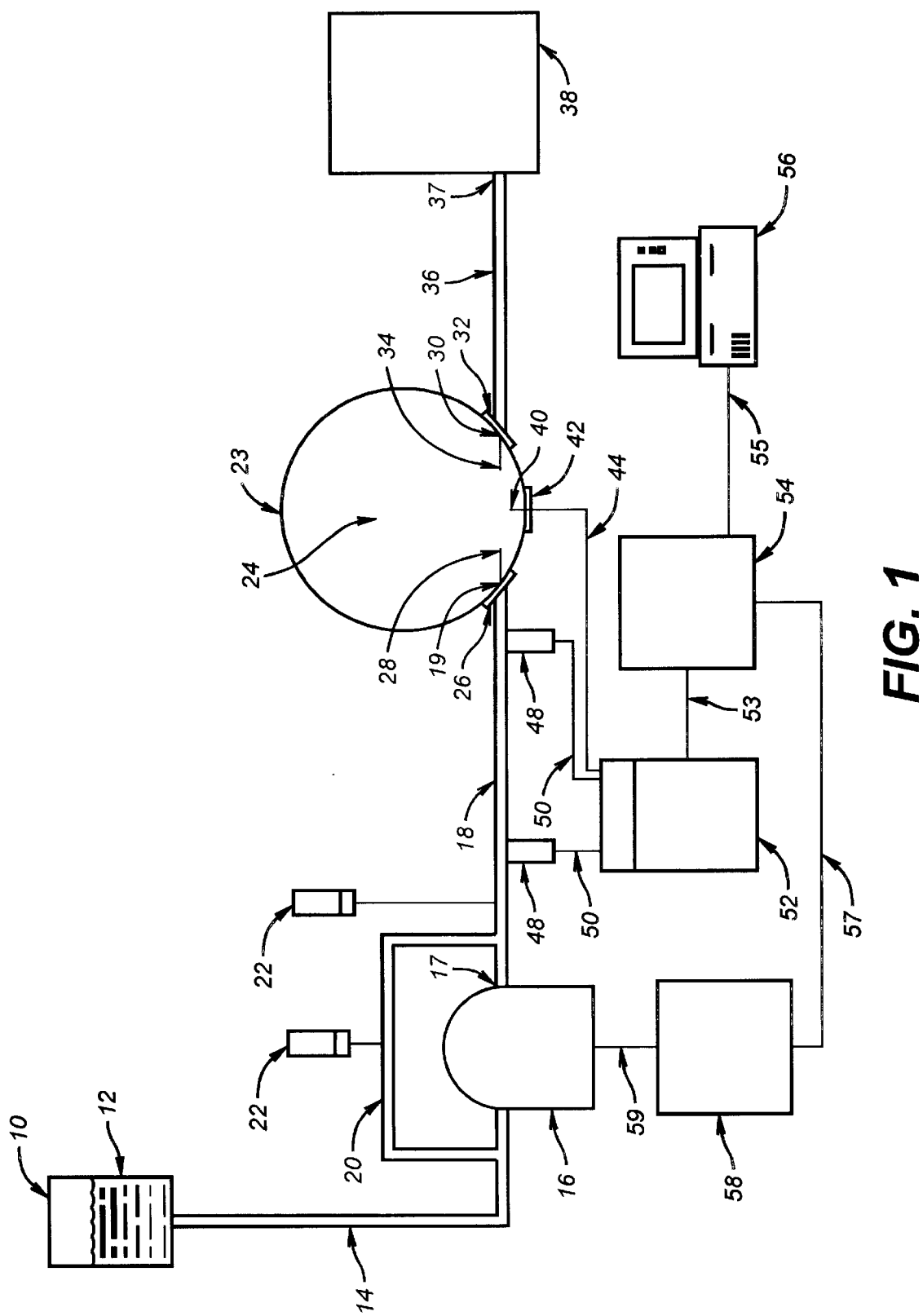
FIG. 1 is a schematic diagram of the irrigation apparatus

Referring to FIG. 1, one embodiment of the IFP measurement device is shown. A fluid reservoir 10 containing an appropriate irrigation fluid 12, such as saline, is in fluid communication with the pump inlet line 14. The pump inlet line 14 provides fluid to the controllable pump 16, which provides pressurization to the infusion line 18. The infusion line comprises a first infusion line end 17 and a second infusion line end 19. A return line 20 is in fluid communication with both the pump inlet line 14 and the infusion line 18. The return line 20 buffers pressure fluctuations in the infusion line 18 and provides a source of hydrostatic pressure from the fluid reservoir 10 in the event of a pump failure. Compliance chambers 22 are in fluid communication with the infusion line 18 and the return line 20 to reduce pressure fluctuations from sources such as the pump rollers.

Figure 3:
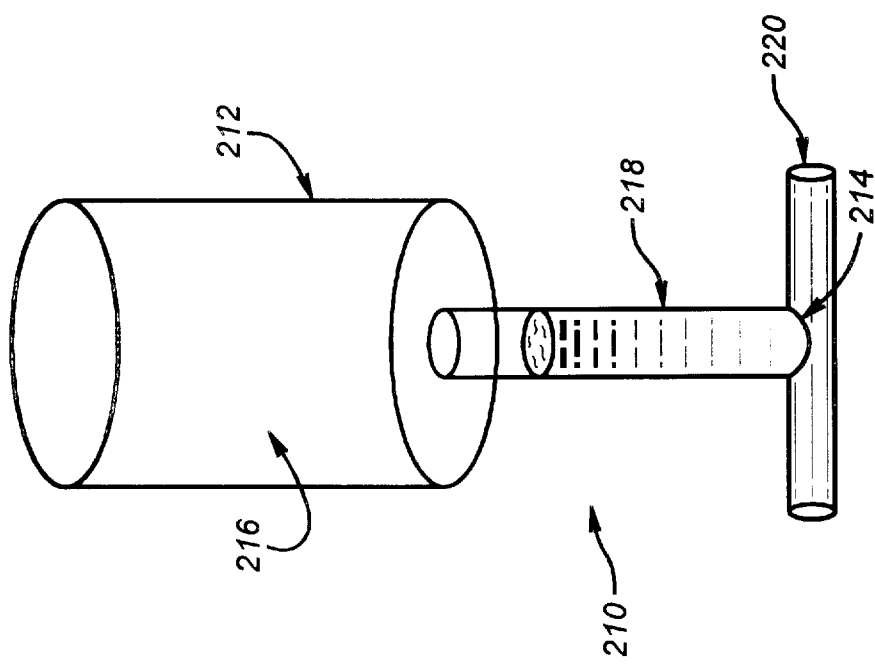
FIG. 3 is a schematic diagram of a compliance chamber.

A typical compliance chamber connected to the infusion line is depicted schematically in FIG. 3. The compliance chamber 210 comprises a vessel 212 which is sealed except for an inlet 214. A volume of air 216 is trapped inside the compliance chamber 210 by a column of fluid 218 which is in fluid communication with the fluid in the infusion line 220. Thus, the column of fluid 218 acts as a damping mass for pressure fluctuations in the infusion line 220.

Referring again to FIG. 1, the object of the irrigation procedure is a body cavity 23. The infusion line 18 extends to the interior of the body cavity 24 through a first incision 26. The infusion line 18 comprises an outlet 28 in fluid communication with the infusion line 18, located at the second infusion line end 19. The outlet 28 extends into the body cavity 24 to allow the irrigation fluid 12 to flow into the interior of the body cavity 24. A portion of the infusion line 18 may also extend into the body cavity 24 to provide proper positioning of the outlet 28.

An aspiration line 36 comprises a first aspiration line end 30 and a second aspiration line end 37. The aspiration line 36 also comprises an inlet 34 in fluid communication with the aspiration line 36, located at the first aspiration line end 30. The inlet 34 extends into the interior of the body cavity 24 through a second incision 32. A portion of the aspiration line 36 may also extend into the interior of the body cavity 24 to provide proper positioning of the inlet 34. The aspiration line 36 is in fluid communication with the surgical machine 38 which provides a vacuum source for aspiration.

To determine the values of the fitting parameters a and b, IFP data is obtained by inserting a pressure transducer 40 into the interior of the body cavity 24 through a third incision 42. Data from the pressure transducer 40 is transmitted via a data line 44 to an electronic filter 46. Two additional pressure transducers 48 are connected to the infusion line 18 to measure the pressure of the irrigation fluid 12 inside the infusion line 18. Data from the pressure transducers 48 are transmitted to the electronic filter 46 via data lines 50. Suitable pressure transducers are the Millar Mikro-Tip Catheter Transducers, produced by Millar Instruments, Houston, Tex. For cost reasons, the model PX TrueWave transducer produced by Baxter Healthcare Corporation, 17221 Red Hill Ave., Irvine, Calif. 92714 is preferred. However, the Baxter transducers are not suitable for use as pressure transducer 40 if a catheter transducer is required for proper positioning within the body cavity 24. The electronic filter 46 comprises a low-pass filter and anti-alias protection. A suitable electronic filter is the IO-Tech DBK-18 low pass filter board. This board has a third-order Butterworth low-pass filter which was found suitable for use in this invention.

The electronic filter 46 is in electronic communication with a Analog-to-Digital ("A/D") converter 52. A suitable A/D converter for this use is the IO-Tech 216A produced by IOtech, Inc., Cleveland, Ohio. The digitalized pressure measurements are transmitted electronically to a programmable digital controller board 54 via cable 53. The digitalized pressure measurements are also transmitted electronically from the programmable digital controller board 54 to a computer 56 via cable 55 for storage, analysis, and display. A suitable computer for use in this invention is a 66 MHz 80486-based PC, with an ISA bus which is compatible with the IO-Tech 216A. The programmable digital controller board 54 is used to send control signals via an electrical connection 57 to the pump speed controller 58, which is electrically connected via electrical connection 59 to the controllable pump 16.

To determine the value of the fitting parameters a and b in accordance with Equation (3), the body cavity 23 shown in FIG. 1 is a test cavity. The computer 56, programmable digital controller board 54, and the pump speed controller 58 are used to provide a control signal to the controllable pump 16. For example, a stair-step signal can be used to step the controllable pump 16 through the maximum expected operating pressure range of 0–200 mmHg. Simultaneous readings from the pressure transducers 40 and 48 provide a data set of values of $P_{up}$, $P_{down}$, and $P_{ifp}$ which are recorded by the computer 56. Standard numerical fitting techniques are then used to determine the values of the fitting parameters a and b.

Once the fitting parameters a and b are known, the apparatus shown in FIG. 1 can be used to measure the IFP during irrigation procedures on an actual body cavity. In this case, the pressure transducer 40, incision 42, and data line 44 are not present. Data from pressure transducers 48 are analyzed by the computer 56 to determine the IFP, $P_{ifp}$, in accordance with Equation (3). The IFP is maintained at a desired set-point by the computer 56 through the programmable digital controller board 54 and the pump speed controller 58 to set the speed of the controllable pump 16. If it is desirable during the irrigation procedure to change the IFP, for example to raise the IFP momentarily to control bleeding, manual input to the computer 56 will provide the computer with a new pressure set-point.

Figure 2:
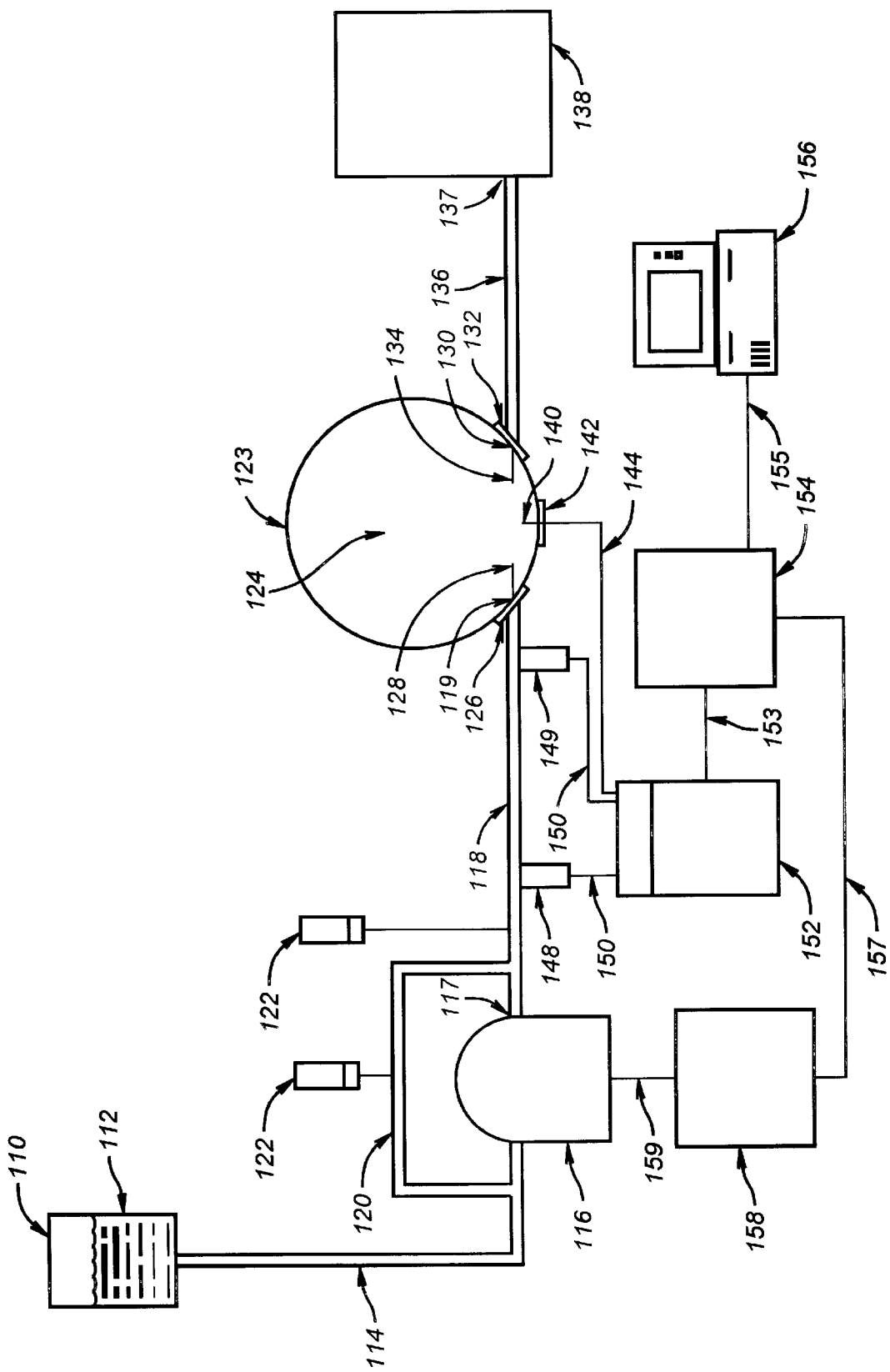
FIG. 2 is a schematic diagram of an alternative embodiment of the irrigation apparatus

Referring to FIG. 2, an alternative embodiment of the IOP measurement and control device is shown. A fluid reservoir 110 containing an appropriate irrigation fluid 112, such as saline, is in fluid communication with the pump inlet line 114. The pump inlet line 114 provides fluid to the controllable pump 116, which provides pressurization to the infusion line 118. The infusion line comprises a first infusion line end 117 and a second infusion line end 119. A return line 120 is in fluid communication with both the pump inlet line 114 and the infusion line 118. The return line 120 buffers pressure fluctuations in the infusion line 118 and provides a source of hydrostatic pressure from the fluid reservoir 110 in the event of a pump failure. Compliance chambers 122 are in fluid communication with the infusion line 118 and the return line 120 to reduce pressure fluctuations from sources such as the pump rollers.

The object of the irrigation procedure is a body cavity 123. The infusion line 118 extends into the interior of the body cavity 124 through a first incision 126. The infusion line 118 comprises an outlet 128 in fluid communication with the infusion line 118, located at the second infusion line end 119. The outlet 128 extends into the body cavity 124 to allow the irrigation fluid 112 to flow into the interior of the body cavity 124. A portion of the infusion line 118 may also extend into the body cavity 124 to provide proper positioning of the outlet 128.

An aspiration line 136 comprises a first aspiration line end 130 and a second aspiration line end 137. The aspiration line 136 also comprises an inlet 134 in fluid communication with the aspiration line 136, located at the first aspiration line end 130. The inlet 134 extends into the interior of the body cavity 124 through a second incision 132. A portion of the aspiration line 136 may also extend into the interior of the body cavity 124 to provide proper positioning of the inlet 134. The aspiration line 136 is in fluid communication with the operations machine 138 which provides a vacuum source for aspiration.

To determine the values of the fitting parameters c and d, IFP data is obtained by inserting a pressure transducer 140 into the interior of the body cavity 124 through a third incision 142. Data from the pressure transducer 140 is transmitted via a data line 144 to an electronic filter 146. A pressure transducer 148 and a flow rate measurement sensor 149 are connected to the infusion line 118 to measure the pressure and flow rate of the irrigation fluid 112 inside the infusion line 118. Pressure transducer 148 and flow rate measurement sensor 149 may be placed at the same or at different locations along the infusion line 118. Data from the pressure transducer 148 and the flow rate measurement sensor 149 are transmitted to the electronic filter 146 via data lines 150. The electronic filter 146 comprises a low-pass filter and anti-alias protection.

The electronic filter 146 is in electronic communication with a Analog-to-Digital ("A/D") converter 152. The digitalized pressure measurements are transmitted electronically to a programmable digital controller board 154 via cable 153. The digitalized pressure measurements are also transmitted electronically from the programmable digital controller board 154 to a computer 156 via cable 155 for storage, analysis, and display. The programmable digital controller board 154 is used to send control signals via an electrical connection 157 to the pump speed controller 158, which is electrically connected via electrical connection 159 to the controllable pump 116.

To determine the value of the fitting parameters c and d in accordance with Equation (5), the body cavity 123 shown in FIG. 2 is a test cavity. The computer 156, programmable digital controller board 154, and the pump speed controller 158 are used to provide a controlled signal to the controllable pump 116. For example, a stair-step signal can be used to step the controllable pump 116 through the maximum expected operating pressure range of 0–200 mmHg. Simultaneous readings from the pressure transducers 140 and 148 and the flow rate sensor 149 provide a data set of values of $P_0$, I, and $P_{ifp}$ which are recorded by the computer 156. Standard numerical fitting techniques are then used to determine the values of the fitting parameters c and d.

Once the fitting parameters c and d are known, the surgical apparatus shown in FIG. 2 can be used to control pressure during irrigation procedures on an actual body cavity. In this case, the pressure transducer 140, incision 142, and data line 144 are not present. Data from pressure transducer 148 and the flow rate sensor 149 are analyzed by the computer 156 to determine the IFP, $P_{ifp}$, in accordance with Equation (5). The IFP is maintained at a desired set-point by the computer 156 through the programmable digital controller board 154 and the pump speed controller 158 to set the speed of the controllable pump 116. If it is desirable during surgery to change the IFP, for example to raise the IFP momentarily to control bleeding, manual input to the computer 156 will provide the computer with a new pressure set-point.

I claim:

1. A device for noninvasively measuring the internal fluid pressure of a body cavity during irrigation procedures on the body cavity comprising:

a source of irrigation fluid;

an infusion line in fluid communication with said source of irrigation fluid and adapted to be in fluid communication with the interior of the body cavity;

a first sensor connected to said infusion line, wherein said first sensor generates a signal relative to the irrigation fluid pressure within said infusion line at the position of said first sensor;

a second sensor connected to the infusion line, wherein said second sensor generates a signal relative to the irrigation fluid pressure within said infusion line at the position of said second sensor; and a computation device in signal communication with said first sensor and said second sensor, wherein said computation device dynamically computes the internal fluid pressure of the body cavity based on said signals from said first sensor and said second sensor.

2. The device of claim 1, wherein said signals from said first sensor and said second sensor are electronic.

3. The device of claim 2, additionally comprising
an electronic filter in electronic communication with said first sensor and in electronic communication with said computation device.

4. The device of claim 2, additionally comprising
an electronic filter in electronic communication with said second sensor and in electronic communication with said computation device.

5. The device of claim 2, additionally comprising
an analog to digital converter in electronic communication with said first sensor and in electronic communication with said computation device.

6. The device of claim 2, additionally comprising
an analog to digital converter in electronic communication with said second sensor and in electronic communication with said computation device.

7. The device of claim 1, wherein said computation device additionally generates a control signal relative to the difference between the dynamically computed internal fluid pressure and a desired internal fluid pressure.

8. The device of claim 1, wherein said body cavity subject to the irrigation procedure is the vitreous cavity of an eye.

9. The device of claim 1, wherein said body cavity subject to the irrigation procedure is the anterior segment cavity of an eye.

10. The device of claim 1, wherein said body cavity subject to the irrigation procedure is a portion of a spinal column.

11. The device of claim 1, wherein the body cavity subject to the irrigation procedure is a peritoneal cavity.

12. A method for noninvasively measuring the internal fluid pressure of a body cavity during irrigation procedures on the body cavity comprising:

providing a source of irrigation fluid;

providing an infusion line in fluid communication with the source of irrigation fluid;

providing fluid communication from said infusion line to the interior of a body cavity;

connecting a first sensor to said infusion line, wherein said first sensor generates a signal relative to the irrigation fluid pressure within said infusion line at the position of said first sensor;

connecting a second sensor to said infusion line, wherein said second sensor generates a signal relative to the irrigation fluid pressure in said infusion line at the position of said second sensor; and computing the internal fluid pressure in said body cavity based on said signals from said first sensor and said second sensor.

13. The method of claim 12, wherein said signals from said first sensor and said second sensor are electronic.

14. The method of claim 13, additionally comprising the step of electronically filtering said signal from said first sensor.

15. The method of claim 13, additionally comprising the step of electronically filtering said signal from said second sensor.

16. The method of claim 13, additionally comprising the step of converting said signal from said first sensor from analog to digital.

17. The method of claim 13, additionally comprising the step of converting said signal from said second sensor from analog to digital.

18. The method of claim 12, additionally comprising the step of providing a control signal based on the computed internal fluid pressure in said body cavity.

19. The method of claim 12, additionally comprising the step of providing a control signal based on the difference between the computed internal fluid pressure in said body cavity and a desired internal fluid pressure.

20. A method of controlling intraocular pressure during operations on an eye comprising:

providing a source of irrigation fluid;

providing an infusion line in fluid communication with the source of irrigation fluid;

providing fluid communication from said infusion line to the interior of a body cavity;

connecting a first sensor to said infusion line, wherein said first sensor generates a signal relative to the irrigation fluid pressure within said infusion line at the position of said first sensor;

connecting a second sensor to said infusion line, wherein said second sensor generates a signal relative to the irrigation fluid pressure in said infusion line at the position of said second sensor; and altering the pressure of the irrigation fluid in said infusion line to regulate the internal fluid pressure in said body cavity based on said signals from said first sensor and said second sensor.

21. A device for measuring the internal fluid pressure of a body cavity during irrigation procedures on the body cavity comprising:

a source of irrigation fluid;

an infusion line in fluid communication with said source of irrigation fluid and adapted to be in fluid communication with the interior of the body cavity;

a first sensor connected to said infusion line, wherein said first sensor generates a signal relative to the irrigation fluid pressure within said infusion line at the position of said first sensor;

a second sensor connected to the infusion line, wherein said second sensor generates a signal relative to the irrigation fluid flow rate within said infusion line at the position of said second sensor; and a computation device in signal communication with said first sensor and said second sensor, wherein said computation device dynamically computes the internal fluid pressure of the body cavity based on said signals from said first sensor and said second sensor.

22. The device of claim 21, wherein said signals from said first sensor and said second sensor are electronic.

23. The device of claim 22, additionally comprising
an electronic filter in electronic communication with said first sensor and in electronic communication with said computation device.

24. The device of claim 22, additionally comprising
an electronic filter in electronic communication with said second sensor and in electronic communication with said computation device.

25. The device of claim 22, additionally comprising
an analog to digital converter in electronic communication with said first sensor and in electronic communication with said computation device.

26. The device of claim 22, additionally comprising
an analog to digital converter in electronic communication with said second sensor and in electronic communication with said computation device.

27. The device of claim 21, wherein said computation device additionally generates a control signal relative to the difference between the dynamically computed internal fluid pressure and a desired internal fluid pressure.

28. The device of claim 21, wherein said body cavity subject to the irrigation procedure is the vitreous cavity of an eye.

29. The device of claim 21, wherein said body cavity subject to the irrigation procedure is the anterior segment cavity of an eye.

30. The device of claim 21, wherein said body cavity subject to the irrigation procedure is a portion of a spinal column.

31. The device of claim 21, wherein the body cavity subject to the irrigation procedure is a peritoneal cavity.

32. A method of measuring the internal fluid pressure of a body cavity during irrigation procedures on the body cavity comprising:
providing a source of irrigation fluid;
providing an infusion line in fluid communication with the source of irrigation fluid;
providing fluid communication from said infusion line to the interior of a body cavity;
connecting a first sensor to said infusion line, wherein said first sensor generates a signal relative to the irrigation fluid pressure within said infusion line at the position of said first sensor;
connecting a second sensor to said infusion line, wherein said second sensor generates a signal relative to the irrigation fluid flow rate in said infusion line at the position of said second sensor; and
computing the internal fluid pressure in said body cavity based on said signals from said first sensor and said second sensor.

33. The method of claim 32, wherein said signals from said first sensor and said second sensor are electronic.

34. The method of claim 33, additionally comprising the step of
electronically filtering said signal from said first sensor.

35. The method of claim 33, additionally comprising the step of
electronically filtering said signal from said second sensor.

36. The method of claim 33, additionally comprising the step of
converting said signal from said first sensor from analog to digital.

37. The method of claim 33, additionally comprising the step of
converting said signal from said second sensor from analog to digital.

38. The method of claim 32, additionally comprising the step of
providing a control signal based on the computed internal fluid pressure in said body cavity.

39. The method of claim 32, additionally comprising the step of
providing a control signal based on the difference between the computed internal fluid pressure in said body cavity and a desired internal fluid pressure.

40. A method of controlling intraocular pressure during operations on an eye comprising:
providing a source of irrigation fluid;
providing an infusion line in fluid communication with the source of irrigation fluid;
providing fluid communication from said infusion line to the interior of a body cavity;
connecting a first sensor to said infusion line, wherein said first sensor generates a signal relative to the irrigation fluid pressure within said infusion line at the position of said first sensor;
connecting a second sensor to said infusion line, wherein said second sensor generates a signal relative to the irrigation fluid flow rate in said infusion line at the position of said second sensor; and
altering the pressure of the irrigation fluid in said infusion line to regulate the internal fluid pressure in said body cavity based on said signals from said first sensor and said second sensor.

* * * * *